US012637643B2

(12) United States Patent
Boudier et al.

(10) Patent No.: US 12,637,643 B2
(45) Date of Patent: May 26, 2026

(54) REACTOR HAVING AN OPTIMIZED LIGHTING DEVICE

(71) Applicant: FERMENTALG, Libourne (FR)

(72) Inventors: Philippe Boudier, Cenon (FR); Francois Godart, Vayres (FR)

(73) Assignee: FERMENTALG, Libourne (FR)

( * ) Notice: Subject to any disclaimer, the term of this patent is extended or adjusted under 35 U.S.C. 154(b) by 916 days.

(21) Appl. No.: 17/799,535

(22) PCT Filed: Feb. 12, 2021

(86) PCT No.: PCT/EP2021/053401
§ 371 (c)(1),
(2) Date: Aug. 12, 2022

(87) PCT Pub. No.: WO2021/160776
PCT Pub. Date: Aug. 19, 2021

(65) Prior Publication Data
US 2023/0113048 A1 Apr. 13, 2023

(30) Foreign Application Priority Data

Feb. 14, 2020 (FR) .................................. FR2001492

(51) Int. Cl.
*C12M 1/00* (2006.01)
*F21V 8/00* (2006.01)
*G02B 5/02* (2006.01)

(52) U.S. Cl.
CPC ........... *C12M 21/02* (2013.01); *C12M 29/08* (2013.01); *C12M 41/06* (2013.01); *G02B 5/0268* (2013.01); *G02B 5/0284* (2013.01); *G02B 6/0036* (2013.01)

(58) Field of Classification Search
CPC ...... C12M 21/02; C12M 29/08; C12M 41/06; G02B 5/0268; G02B 5/0284; G02B 6/0036
(Continued)

(56) References Cited

U.S. PATENT DOCUMENTS 3,986,297 A 10/1976 Ichimura et al.
4,456,512 A 6/1984 Bieler et al.
(Continued)

FOREIGN PATENT DOCUMENTS

CN 201501874 U 6/2010
FR 1050015 A 1/1954
(Continued)

OTHER PUBLICATIONS

Dongzhe Sun, b, Zhao Zhanga, b, Xuemei Maoa, b, Tao Wua, b, Yue Jiangc, Jin Liua, b, Feng Chena, b, Light enhanced the accumulation of total fatty acids (TFA) and docosahexaenoic acid (DHA) in a newly isolated heterotrophic microalga *Crypthecodinium* sp. SUN. Bioresource Technology, vol. 228, Mar. 2017, p. 227-234.

*Primary Examiner* — Michael L Hobbs
*Assistant Examiner* — Lenora A Abel
(74) *Attorney, Agent, or Firm* — BCF LLP

(57) ABSTRACT

The present invention relates to a reactor comprising a vessel (1) for containing: •a mass to be treated, and •at least one lighting device (2a, 2b) intended to promote the treatment of said mass, characterized in that each lighting device (2a, 2b) comprises a light diffuser including at least one micro-etched plate (211) which is transparent to light radiation.

20 Claims, 5 Drawing Sheets

(58) Field of Classification Search
USPC ....................................................... 435/292.1
See application file for complete search history.

(56) References Cited

U.S. PATENT DOCUMENTS

| | | | |
|---|---|---|---|
| 5,162,051 A | 11/1992 | Hoeksema | |
| 7,824,904 B1 | 11/2010 | Dimanshteyn | |
| 2004/0101449 A1 | 5/2004 | Marchant et al. | |
| 2009/0126265 A1 | 5/2009 | Rasmussen et al. | |
| 2009/0134173 A1 | 5/2009 | Liang et al. | |
| 2010/0005711 A1 | 1/2010 | Mcneff | |
| 2010/0190227 A1 | 7/2010 | Dauth et al. | |
| 2010/0311156 A1 | 12/2010 | Beliaev et al. | |
| 2012/0088278 A1 | 4/2012 | Kim et al. | |
| 2013/0045531 A1* | 2/2013 | Weaver .................. | G02B 6/001 |
| | | | 435/292.1 |

FOREIGN PATENT DOCUMENTS

| | | | |
|---|---|---|---|
| FR | 3004724 | A1 | 10/2014 |
| JP | 2004084883 | A | 3/2004 |
| JP | 2012183002 | A | 9/2012 |
| KR | 101043583 | B1 | 6/2011 |
| WO | 2002089053 | A1 | 11/2002 |
| WO | 2008104599 | A1 | 9/2008 |
| WO | 2008145719 | A1 | 12/2008 |
| WO | 2009018498 | A2 | 2/2009 |
| WO | 2009069967 | A2 | 6/2009 |
| WO | 2010014010 | A2 | 2/2010 |
| WO | 2010089151 | A1 | 8/2010 |
| WO | 2011012714 | A2 | 2/2011 |
| WO | 2011154886 | A1 | 12/2011 |
| WO | 2014174182 | A1 | 10/2014 |
| WO | 2016083548 | A1 | 6/2016 |
| WO | 2017050917 | A1 | 3/2017 |

* cited by examiner

4/5

REACTOR HAVING AN OPTIMIZED LIGHTING DEVICE

CROSS-REFERENCE TO RELATED APPLICATIONS

This application is a national phase filing under 35 U.S.C. 371 of International Application No. PCT/EP2021/053401 filed on Feb. 12, 2021, which claims the benefit of French Patent Application No. FR2001492, filed on Feb. 14, 2020. The contents of the aforementioned applications are incorporated by reference in their entirety herein.

FIELD OF THE INVENTION

The present invention relates to the general technical field of reactors with integrated lighting, in particular for the culture of photosensitive microorganisms.

It can be a bioreactor but also a chemical or physico-chemical reactor.

BACKGROUND OF THE INVENTION

The concept of bioreactor, or biological reactor, designates here a reactor within which biological phenomena develop, such as growth of cultures of pure microorganisms or of a consortium of microorganisms (in particular microalgae), in very varied fields such as the treatment of effluents, the production of biomass containing biomolecules of interest (that is to say biomolecules whose valorization is known). This notion therefore encompasses in particular reactors called fermenters. A bioreactor typically comprises a (cylindrical or parallelepipedal) vessel containing a culture medium for biological species (yeasts, bacteria, microscopic fungi, algae, animal and plant cells) for:

the production of biomass, or for
the production of a metabolite, or for
the bioconversion of a molecule of interest.

Various types of operating conditions may be necessary for the growth of biological species within such a bioreactor; in particular, light-delivery autotrophic (or photo-auto-trophic) growth (also called photosynthesis) or mixotrophic growth (with a combined input of carbon source and light) regimes are thus known. It should also be noted that light can act on cell metabolism by inducing or suppressing the production of certain compounds, independently of growth and photosynthesis. A supply of light during culture can therefore be useful even when the microorganisms are heterotrophic.

In the following, particular focus will be given to photo-bioreactors, that is to say bioreactors in which a supply of light (continuous, cyclically, or in the form of pulses) is implemented. Photo-bioreactors in which the supply of light is carried out from the inside of the vessel have already been proposed. Document U.S. Pat. No. 3,986,297 proposes in particular a photo-bioreactor in which the supply of light is produced by immersion, in the culture medium, of illumination means (such as xenon lamps). A disadvantage of this solution is that the efficiency of the photo-bioreactor is inversely proportional to its dimensions. Thus, the more the dimensions of the photo-bioreactor increase, the more its efficiency decreases.

Provision has also been made of photo-bioreactors in which light is supplied from the outside of the vessel. In particular, a well-controlled configuration consists in providing the vessel with windows allowing the penetration of light generated from the outside of the vessel (natural or artificial light). A disadvantage of such a configuration is that the windows limit the illumination surface and absorb or reflect a significant part of the photons emitted by the lighting source.

Whether the light supply is made from the inside or the outside of the vessel, the productivity of a photo-bioreactor (production of biomass per unit volume) is directly related to its specific surface (ratio of illuminated surface to culture volume). It is therefore necessary for the photo-bioreactor to have a large illuminated specific surface.

Whether they are flat or cylindrical, a disadvantage of current photo-bioreactors is that they must occupy a large floor surface for their productivity to be acceptable.

Moreover, regardless of the light source chosen to illuminate the culture medium (Neons, LEDs, Natural Light), its photonic energy supply is carried out in a very localized manner, so that:

most of the photons emitted by the light source cannot be biologically consumed by the microorganism due to an energy overload, the dissipation of the heat generated by the light source is poorly controlled, it is complex and expensive to produce large photo-bioreactors.

A purpose of the present invention is to provide an economical photo-bioreactor, both in terms of investments and operating costs, and whose land area is reduced.

Another purpose of the invention is to provide a large capacity photo-bioreactor (vessel of 1000 liters or more) in which the amount of photon yield ($\mu$mol-ph-s$^{-1}$) provided by a luminous surface per power unit (Watt) is optimized.

BRIEF DESCRIPTION OF THE INVENTION

To this end, the invention proposes a reactor including a vessel for containing:

a mass to be treated, and at least one lighting device intended to promote the treatment of this mass, remarkable in that each lighting device comprises:

a light diffuser, the diffuser including at least one micro-etched plate which is transparent to light radiation, said plate having opposite rear and front faces and at least two edges between the rear and front faces, the area of each face being greater than the area of each edge, the rear face including a plurality of micro-patterns, a light source to generate the light radiation, the light source being disposed on at least one edge of the plate and being oriented so that the light radiation it generates propagates in the plate.

This solution allows to obtain a photo-bioreactor with better yields (energy on the one hand, and biomass production on the other) than existing photo-bioreactors.

Indeed, the use of one (or more) micro-etched plate(s) allows the homogeneous conduction of the light radiation generated by the light source. The photon energy is guided through the entire micro-etched plate and emerges therefrom over the entire surface of its front face, which improves the ratio of illuminated surface to illuminated volume directly in contact with the culture medium. Thus, the invention allows to increase the ratio $\mu$mol-photons s$^{-1}$ W$^{-1}$ per unit volume, which ensures a reduction in the environmental impact of the photo-bioreactor and reduces the costs associated with its operation.

Preferred but non-limiting aspects of the assembly according to the invention are the following:

each plate may be substantially flat and comprise four
   edges, each light source including a plurality of light-
   emitting diodes disposed on at least one of the smallest
   edges;
each plate may be cylindrical and comprise two edges,
   each light source including a plurality of light-emitting
   diodes disposed on at least one of the two edges;
the diodes of the plurality of light-emitting diodes can be
   disposed on the edge of the plate furthest from the
   bottom of the vessel;
each light diffuser can comprise a pair of micro-etched
   plates arranged so that their rear faces extend opposite
   one another;
each light diffuser may further comprise at least one layer
   of material reflecting the light radiation, each layer of
   reflective material extending over the rear face of a
   respective plate;
each light diffuser may further comprise at least one
   transmission layer, each layer of transmission material
   extending over the front face of a respective plate;
the reactor may comprise a plurality of light diffusers, two
   adjacent light diffusers being spaced apart by a distance
   comprised between 2 and 10 centimeters, preferably
   between 4 and 8 centimeters, and even more preferably
   substantially equal to 6 centimeters;
the light source of each lighting device can be adapted to
   generate a continuous light radiation;
the reactor may comprise a plurality of light diffusers, two
   adjacent light diffusers being spaced apart by a distance
   comprised between 8 and 150 centimeters, preferably
   between 10 and 50 centimeters, and even more pref-
   erably substantially equal to 11 centimeters;
the light source of each lighting device can be adapted to
   generate discontinuous light radiation in the form of
   flashes composed of alternating dark phases and illu-
   minated phases, for example at a frequency comprised
   between 10 and 50 KHz;
the vessel can have a capacity of 100 $m^3$, the surface
   covered by the plates of the light diffusers being
   comprised between 2000 and 3000 $m^2$, preferably
   between 2250 and 2750 $m^2$, preferably substantially
   equal to 2500 $m^2$;
the lighting devices can consist of:
   a first group of lighting devices with a first height, and
   a second group of lighting devices with a second height
     lower than the first height, a lighting device of the
     second group being disposed between two succes-
     sive lighting devices of the first group;
the reactor may further comprise an injection system
   including a plurality of diffusion units, each diffusion
   unit:
   extending between two adjacent light diffusers, and
   being separated from the other diffusion units by at
     least two successive light diffusers;
each lighting device can be independently connected to an
   electrical power supply module so that each lighting
   device can be removed individually from the reactor
   during its operation.

BRIEF DESCRIPTION OF THE DRAWINGS

Other advantages and features of the reactor according to
the invention will emerge better from the following descrip-
tion of several variant embodiments, given by way of
non-limiting examples, from the appended drawings
in which:

4

Figure 1:
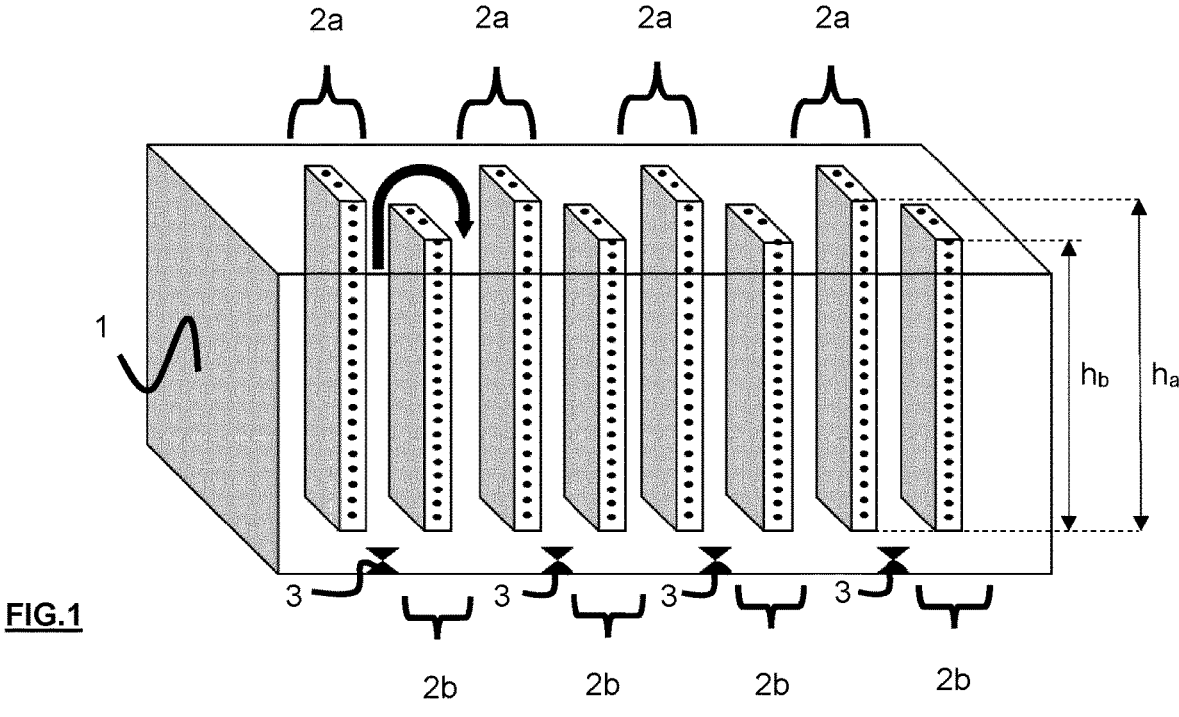
Figure 2:
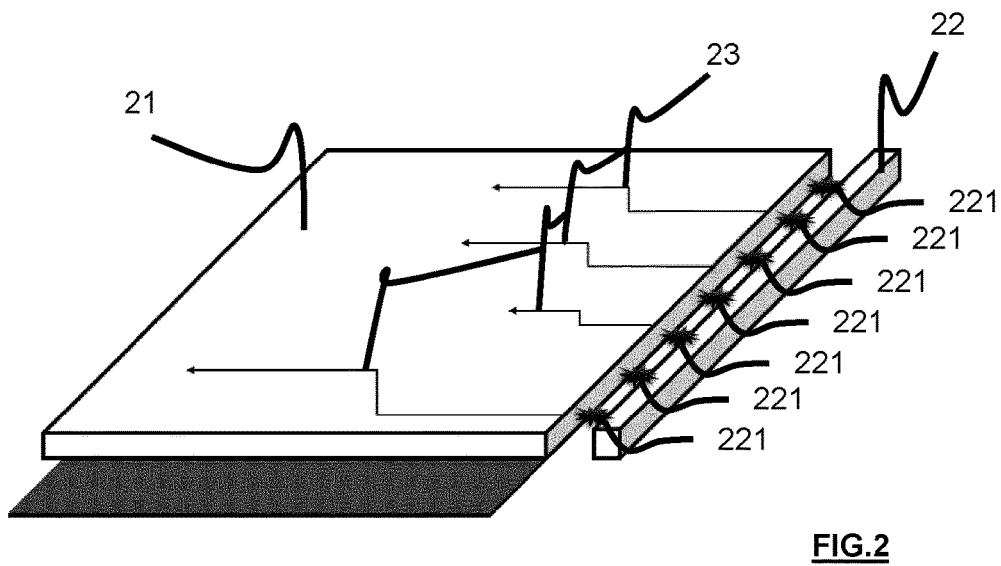
Figure 3:
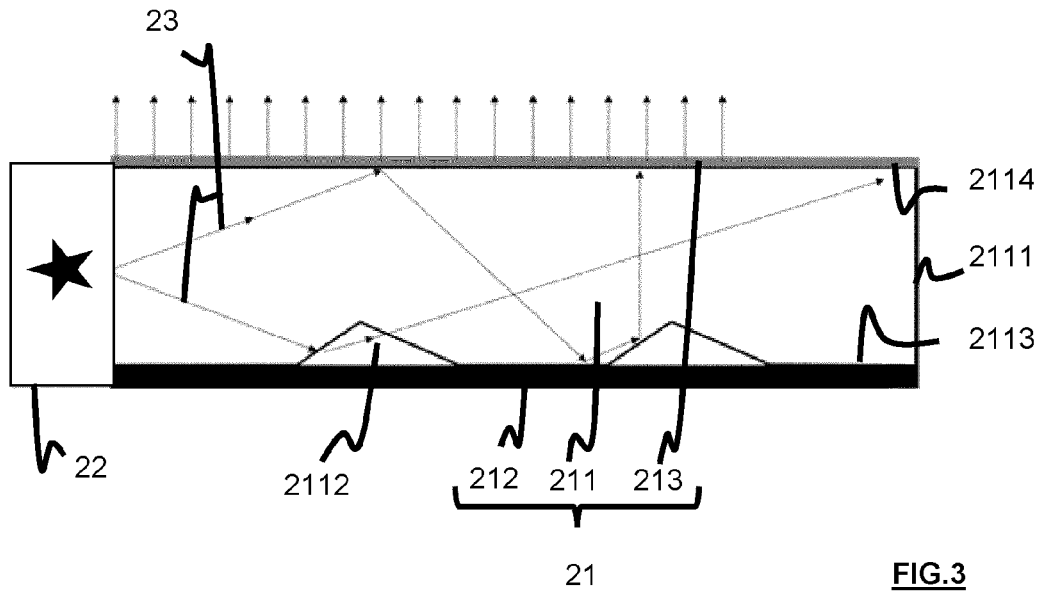
Figure 4:
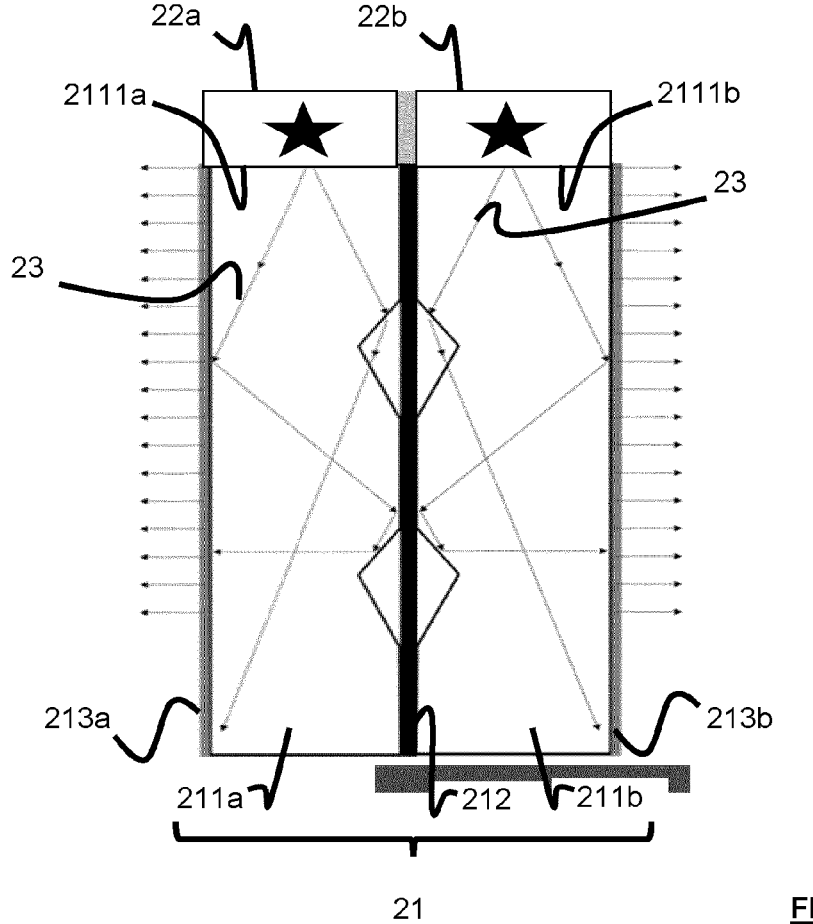
Figure 5:
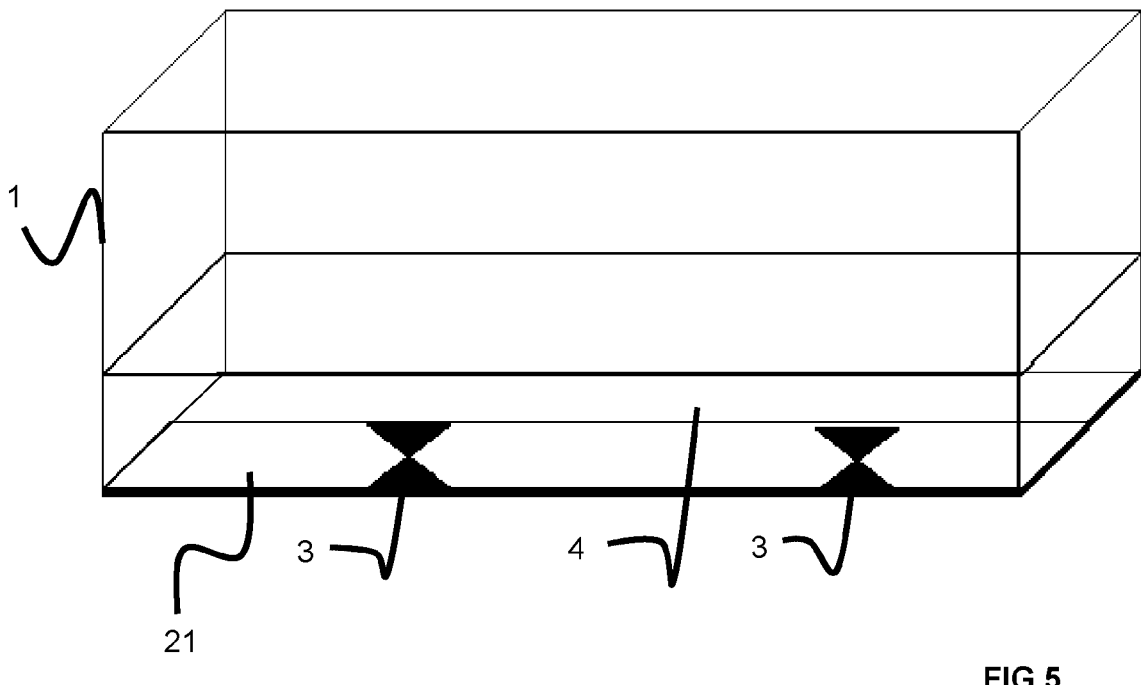
Figure 6:
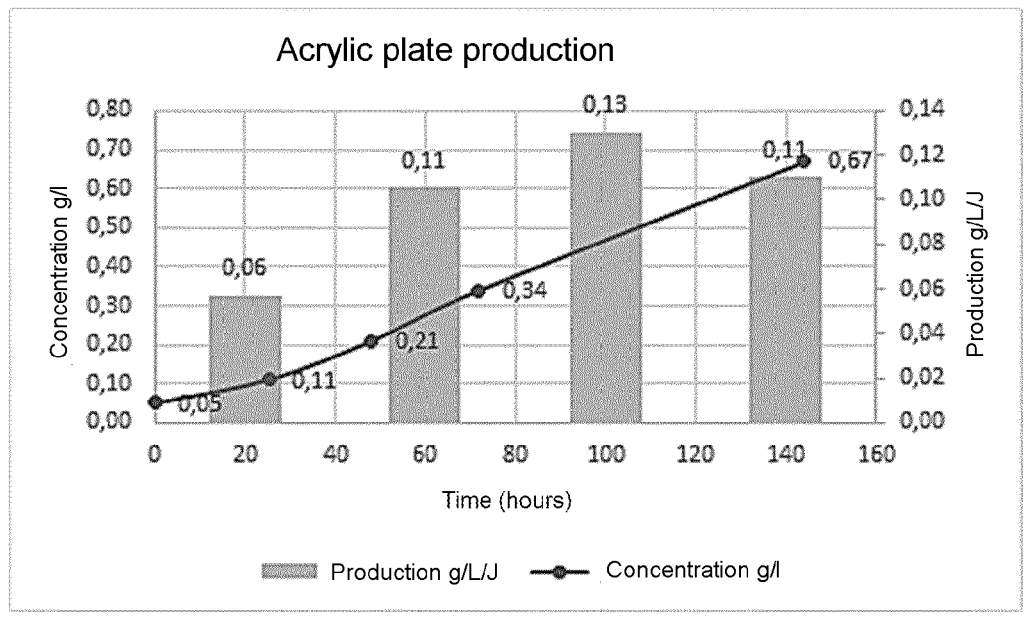
Figure 7:
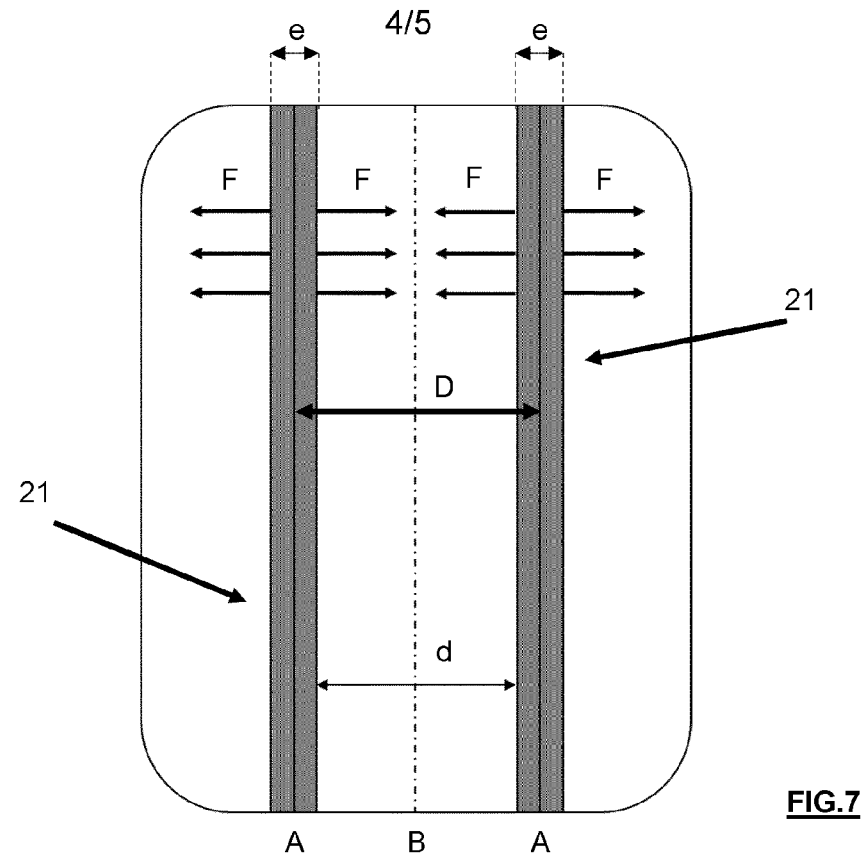
Figure 8:
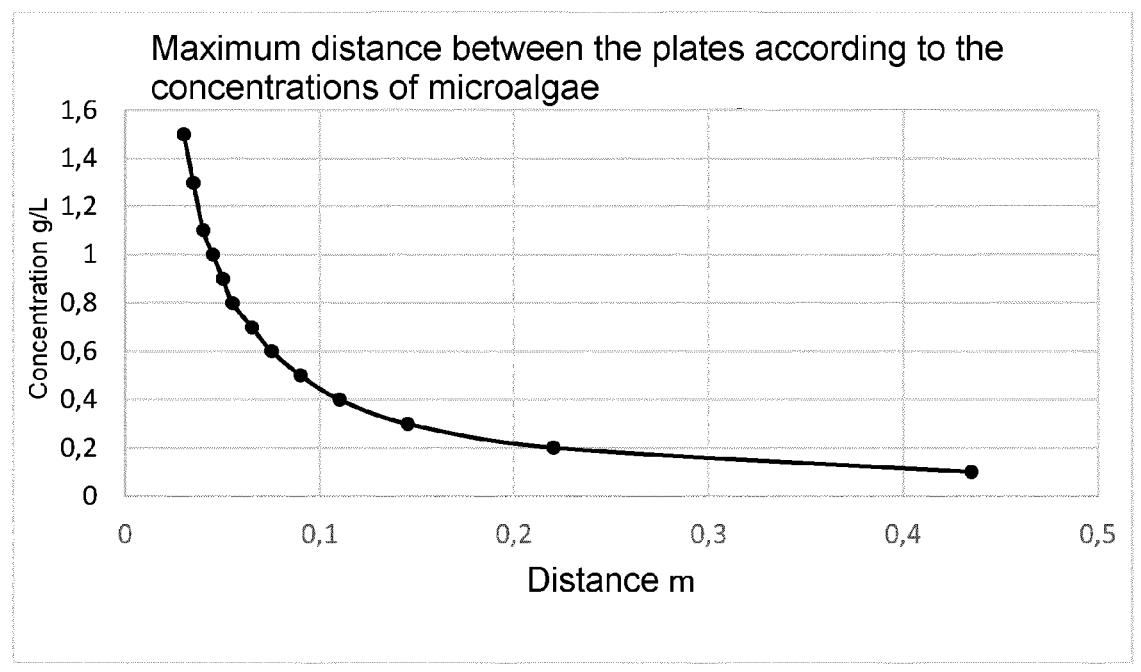
Figure 9:
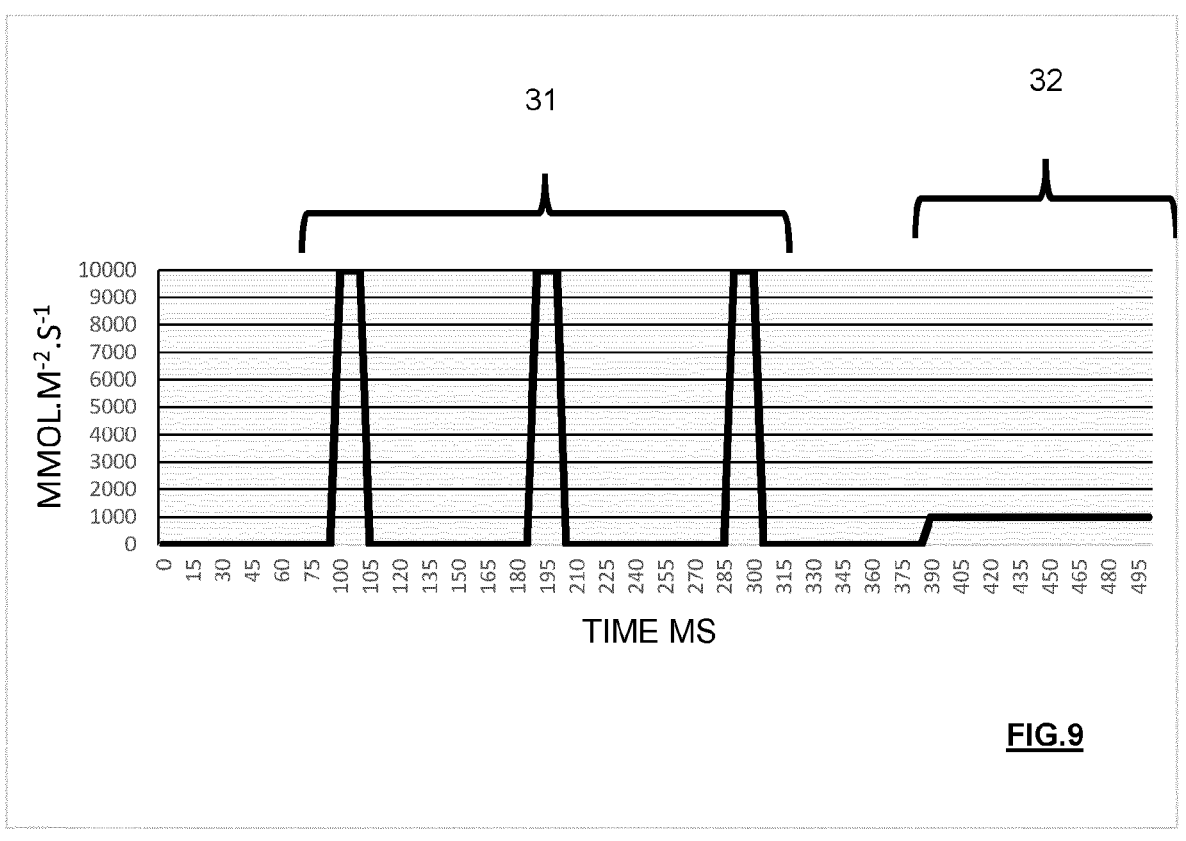
Figure 10:
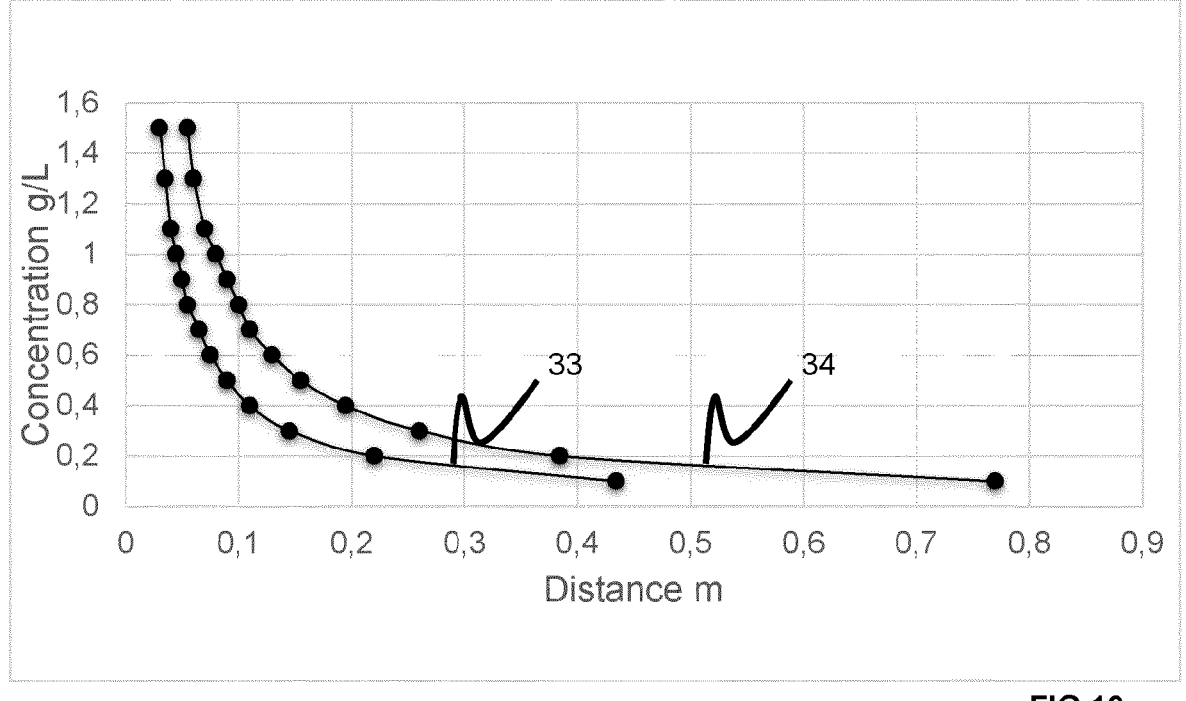

FIG. 1 is a schematic perspective representation of a first
variant of photo-bioreactor according to the invention;
   FIG. 2 is a schematic perspective representation of a
lighting device;
   FIG. 3 is a schematic cross sectional representation of a
first embodiment of the lighting device;
   FIG. 4 is a schematic cross sectional representation of a
second embodiment of the lighting device;
   FIG. 5 is a schematic representation of an experimental
variant of photo-bioreactor;
   FIG. 6 is a curve illustrating the biomass production yield
(as a function of various parameters) obtained from the
experimental variant of photo-bioreactor illustrated in FIG.
5;
   FIG. 7 is a partial cross-sectional view of a second
photo-bioreactor variant;
   FIG. 8 is a curve illustrating the maximum concentration
of microalgae as a function of a distance between two
adjacent lighting devices;
   FIG. 9 is a block diagram illustrating the difference
between continuous lighting and discontinuous lighting;
   FIG. 10 shows microalgae concentration curves as a
function of a distance between two adjacent lighting devices
in the case of continuous lighting on the one hand and in the
case of discontinuous lighting on the other hand.

DETAILED DESCRIPTION OF THE
INVENTION

Various examples of photo-bioreactors according to the
invention will now be described with reference to the
figures. In these various figures, the equivalent elements are
designated by the same reference number.

1. Generalities

Referring to FIG. 1, the bioreactor comprises:
A vessel 1 intended to receive a mass to be treated,
A plurality of lighting devices 2a, 2b, and
An injection system including a plurality of units 3 for
   diffusing carbon dioxide ($CO_2$) in the form of gas
   bubbles or in the form of a fluid consisting of $CO_2$
   dissolved in an aqueous medium.
Each lighting device is intended to be integrated into the
vessel for the treatment of the medium contained in the
vessel. These lighting devices are intended to be fully
immersed in the culture medium. In the following, the
bioreactor will be described with reference to the treatment
of a biomass formed of microorganisms, for example
microalgae. It is however understood that the following
description also applies to other types of reactors, chemical
or physico-chemical reactors.
   As illustrated in FIG. 1, the lighting devices 2a, 2b are
disposed at a non-zero distance from the bottom of the
vessel. The lighting devices 2a, 2b can be of different
heights. In particular, the bioreactor may comprise:
   a first group 2a of lighting devices having a first height $h_a$,
     and
   a second group 2b of lighting devices having a second
     height $h_b$ lower than the first height $h_a$,
a lighting device of the second group 2b being disposed
between two successive lighting devices of the first group
2a. This promotes the mixing and homogenization of the
mass to be treated.
   To further increase mixing and homogenization of the
mass to be treated, the diffusion units 3 of the injection
system can be disposed periodically downstream of each lighting device of the first group 2*a* (the reactor having no diffusion unit 3 downstream of the lighting device of the second group 2*b*). Thus, after having circulated under the lighting device of the first group 2*a*, the mass to be treated is drawn vertically towards the top of the vessel 1 (that is to say direction opposite to the bottom) by the $CO_2$ bubbles (or the fluid containing the dissolved $CO_2$) emitted by the diffusion units 3. The mass to be treated passes over the lighting device of the second group 2*b* and falls back towards the bottom of the vessel by gravity. This creates a circulation of the mass to be treated through the vessel, which improves mixing and homogenization of the mass to be treated. Alternatively, the lighting devices 2*a*, 2*b* of the bioreactor can all be of identical height. This simplifies the installation of lighting devices by an operator. In this case, the diffusion units 3 are disposed every two lighting devices so that two successive diffusion units 3 are separated by two adjacent lighting devices 2*a*, 2*b*.

1.1. Vessel

The vessel 1 is intended to contain the mass to be treated. It comprises a bottom and at least one side wall.

In the embodiment illustrated in FIG. 1, the vessel 1 is substantially parallelepipedal. It is composed of a bottom, four side walls and a ceiling (or lid) which is at least partially removable.

In other embodiments, the vessel 1 can be cylindrical and comprise a lower base forming a bottom, an upper base forming a lid, and a side wall between the lower and upper bases.

The material constituting the walls of the vessel 1 can be stainless steel or equivalent. Of course, other materials can be chosen depending on the intended application (Plexiglass®, Polypropylene, Concrete, etc.). In all cases, the vessel is preferably made of a material resistant to cleaning products (bleach, peroxide, etc.).

1.2. Lighting Device

Referring to FIG. 2, each lighting device 2*a*, 2*b* comprises:

one (or more) light diffuser(s) 21, and one (or more) light source(s) 22.

The light source 22 allows the generation of a luminous flux. The light diffuser 21 allows:

to guide the luminous flux generated by the light source, and to redisperse it in a homogeneous way towards the mass to be treated.

Advantageously, each light source 22 can be independently connected to an electrical power supply module. The module allows to supply the electrical energy necessary for the generation of the luminous flux. The fact that each light source is independently connected to an electrical power supply module allows to individually remove each lighting device 2*a*, 2*b* from the bioreactor during operation of the latter.

1.2.1. Light Diffuser

The light diffuser 21 comprises one (or more) textured plate(s) 211. Each plate 211 can be substantially flat and rectangular (adapted in the case of a parallelepiped vessel) or tubular (adapted in the case of a cylindrical vessel).

Each plate 211 comprises a rear face 2113, a front face 2114 and:

four side ridges (or edges) 2111 in the case of a rectangular plate 211, or two side ridges (or edges) 2111 in the case of a tubular plate 211.

Each side ridge 2111 can be polished, and at least one of the side ridges 2111 is intended to come into contact with the light source 22 to allow the transmission of the luminous flux through the plate 211.

The material constituting each plate 211 can be polymethyl methacrylate (PMMA) or another transparent material known to the person skilled in the art which allows the plate 211 to conduct—by total internal reflection on its front and rear faces—the luminous flux emitted by the light source 22, such as for example:

another transparent methacrylate resin such as methyl methacrylate, ethyl ethacrylate, butyl methacrylate, propyl or isopropyl methacrylate, or a transparent resin of the polystyrene, polycarbonate, polyacrylate type, or a glass/a fused silica.

1.2.1.1. Micro-Patterns

Referring to FIG. 3, each plate 211 comprises a plurality of micro-patterns 2112 on its rear face 2113. The micro-patterns 2112 allow to intercept the radiation 23 of the luminous flux circulating through the plate 211 and to direct them towards the front face 2114 so as to facilitate their transmission out of the plate 211. More specifically, the radiation 23 which strikes each micro-pattern 2112 is redispersed. Each radiation 23 is re-emitted at an angle such that it can leave the plate 211 via the front face 2114 opposite the rear face 2113 including the micro-patterns 2112. Each micro-pattern 2112 can consist of a-point or furrow-cavity having a shape chosen from a conical shape, a (poly) pyramidal shape, a quadrangular shape, or any other shape known to the person skilled in the art and allowing each micro-pattern 2112 to deflect the radiation 23 of the luminous flux. In particular, in the example illustrated in FIG. 3, the micro-patterns 2112 consist of fine grooves parallel to the side ridge 2111 in contact with the light source 22.

Of course, the micro-patterns 2112 can consist of deflection elements other than cavities, such as:

light scattering particles disposed in the material constituting the plate 211, or surface texturing components disposed on the rear face 2113, such as emerging hemispherical structures, bumps extending outward from the rear face 2113, emerged pyramidal structures or combinations comprising at least one of the previous structures.

The height (that is to say dimension along an axis perpendicular to the rear face) of each micro-pattern 2112 can be comprised between 0.15 and 0.5 μm, and the pitch between two adjacent micro-patterns can be comprised between 20 and 900 μm, and in particular greater than or equal to 100 μm.

Advantageously, the micro-patterns 2112 can be disposed on the rear face 2113 according to a consecutive distance inversely proportional to the distance of said micro-patterns 2112 from the side ridge 2111 in contact with the light source 22. Such an arrangement allows to obtain a constant light intensity over the entire surface of the rear face 2113. Indeed, the intensity of the light flux which penetrates the plate 211 decreases depending on its distance relative to the light source 22. By varying the density of micro-patterns 2112 on the rear face 2113, it is possible to compensate for the loss of intensity by increasing the density of micro-patterns 2112.

1.2.1.2. Reflective Layer

The light diffuser 21 may also comprise a layer of material 212 that reflects the light flux.

This layer of reflective material 212 preferably extends over the entire rear face 2113 of the plate 211 including the plurality of micro-patterns 2112.

The layer of reflective material 212 may consist of a film of reflective material such as a metallized aluminum film. Alternatively, the layer of reflective material 212 can consist of a paint made of material with a refractive index lower than that of the material 211 constituting each plate 21.

1.2.1.3. Transmission Layer

The light diffuser 21 may also comprise a transmission layer 213 on the front face 2114 of the plate 211.

This transmission layer 213 allows to promote the transmission of the radiation 23 of the luminous flux towards the outside of the plate 211.

This transmission layer 213 also allows to smooth the illumination effect obtained with the light diffuser 21.

The transmission layer 213 finally allows to protect the plate 21 against possible mechanical attacks (scratches due to friction, etc.).

The transmission layer 213 can for example consist of a protective varnish with a refractive index close to the refractive index of the material constituting the plate 211.

1.2.2. Light Source

Each light source 22 may comprise one (or more) light-emitting diode(s) (LED) 221. Preferably, each diode 221 is a power light-emitting diode (HPLED), that is to say a LED with a power greater than 1 watt. For example, each diode 221 can be a light-emitting diode directly mounted on chips (also known as "COB" LEDs, an acronym for the expression "Chip On Board"). In this case, the light source 22 may include a COB LED module composed of several LED chips fixed to a ceramic substrate (for example). This allows to generate a more powerful and dense luminous flux. The diodes 221 of the light source 22 can be individual, or be disposed "in a strip" or "in a ribbon" (see patent application FR1050015). The use of diodes disposed in a ribbon allows to facilitate the manufacture of the lighting device, each light source 22 being intended to come into contact with a side ridge of the to be disposed on a side ridge 2111 of the plate 211 of the light diffuser 21. The diodes 221 can be supplied with electrical energy via one (or more) connection cable(s) electrically connected to a source of electrical energy.

Regardless of the arrangement chosen, the diodes 221 of the light source 22 can all be identical with the same excitation regime, or be different. In particular, the diodes 221 of a light source 22 can have:

distinct excitation regimes (for example continuous regime for some, and flash regime at a frequency comprised between 1 and 150 kHz for others), and/or distinct emission spectra (for example in white light for some and blue light for others), etc.

Each light source 22 may also comprise one (or more) reflector(s) (not shown) to reflect, orient and focus the light produced by the diodes 221.

Each light source is intended to come into contact with a side ridge of the plate 211 so that the radiation 23 of the luminous flux generated by the light source propagates inside the plate 211. Advantageously, the diodes 221 and the connection cable(s) can be embedded/cast in a resin to seal each light source.

In the embodiment illustrated in FIG. 3, the lighting device comprises a light source 22 intended to come into contact with a side ridge 2111 of the plate 211. Alternatively, each lighting device can comprise two light sources 22 intended to come into contact with a respective opposite side ridge 2111 of the plate 211. Further alternatively, each lighting device may comprise four light sources 22 intended to come into contact with a respective side ridge 2111 of the plate 211.

1.3. Injection System

The injection system supplies the bioreactor with nutrients, in particular $CO_2$. In particular, the injection system allows:

to provide the carbon dioxide necessary for the development of biomass and to suspend the carrier particles of microorganisms contained in the biomass culture medium.

The supply of carbon dioxide can be continuous or discontinuous in response to certain criteria such as time or pH. As stated earlier, carbon dioxide can be introduced:

in the form of gas bubbles, or in the form of an aqueous solution pumped or pushed into the bioreactor.

The introduction of carbon dioxide in the form of gas bubbles allows a better distribution of $CO_2$ in the vessel.

The injection system may comprise:

a $CO_2$ supply unit—such as a booster (in the case of gas $CO_2$) or a pump (of the turbine type in the case of fluid $CO_2$)—preferably equipped with a non-return valve in order to avoid the rise of sludge or effluent at the $CO_2$ supply unit, a plurality of broadcast units 3 forming:

in the case of gas $CO_2$, micro-bubbling heads for the diffusion of bubbles of different diameters, in the case of $CO_2$ dissolved in an aqueous medium, fluid ejection nozzles for the diffusion of the fluid containing dissolved $CO_2$.

The diffusion units can be of different types known to the person skilled in the art, for example diffusers made of microporous composite materials, with a membrane (EPDM, silicone, etc., preferably EPDM), made of ceramic or slotted diffusers, etc.

Each diffusion unit is preferably disposed in the immediate vicinity of the bottom of the vessel. Moreover, each diffusion unit 3 is disposed between two adjacent lighting devices 2a, 2b, the different diffusion units 3 being arranged so that each diffusion unit 3 is surrounded by lighting devices distinct from the lighting devices 2a, 2b surrounding the other diffusion units 3. In other words, each diffusion unit 3 is separated from the nearest diffusion unit 3 (or the nearest units) by two lighting devices 2a, 2b.

1.4. Biomass Processing

The biomass cultured in the reactor according to the invention can be harvested by any technique known to the person skilled in the art such as sedimentation, filtration, flotation or centrifugation techniques.

The biomass harvest can be implemented continuously or semi-continuously, in particular in the case where the bioreactor is installed on an industrial site. For this purpose, the bioreactor can be associated with a separation unit—decanter and/or centrifuge and/or filter etc.—allowing a portion of the contents of the vessel to be taken to separate the biomass from the culture medium.

The biomass thus extracted can then be packaged (vacuum freezing, etc.) for subsequent use. The culture medium, once separated from the biomass, can be reintroduced into the vessel of the bioreactor.

1.5. Other Features of the Bioreactor

The reactor can also comprise a control module including one (or more) sensor(s) to check the parameters of the bioreactor. In particular, the control module may comprise:

one (or more) pH probe(s),
one (or more) sensor(s) for measuring the $CO_2$ level,
one (or more) light sensor(s),
one (or more) $PO_{3/4}$, and/or $NO_3$, and/or $NH_4$ sensor(s),
one (or more) temperature sensor(s).

The various sensors and probes of the control module allow to maintain optimal values for the parameters of the bioreactor influencing the growth of the biomass.

In particular, the control module can adapt the amount of $CO_2$ injected into the culture medium according to the measurements made by the pH probe and/or by the sensor(s) for measuring the $CO_2$ level, etc. For example, if the measured $CO_2$ level is below a threshold, the control module can order the injection of a greater amount of $CO_2$ into the vessel (relative to a target amount). Conversely, if the measured pH is below a predetermined threshold, the control module can control the injection of a lower amount of $CO_2$ (relative to a target amount).

Similarly, if the measured temperature is lower (respectively higher) than a threshold temperature, the control module can control the activation of a heat exchanger—such as a plate heat exchanger—integrated into the bioreactor vessel to heat (respectively cool) the culture medium.

Also, depending on the measurements taken by the $PO_{3/4}$, $NO_3$, $NH_4$ sensor(s), the control module can adapt an amount of nutrient (phosphorus, nitrogen, etc.) injected into the culture medium (by acting on the activation/deactivation of a pump connected to a source of nutrients, etc.).

Finally, the measurement of information representative of the luminosity inside the culture medium allows an estimation of the biomass concentration inside the vessel. Thus, it is possible to regulate the biomass harvesting step. In particular, if the light measurement inside the vessel is representative of a too low biomass concentration, the control module can suspend biomass harvesting. Conversely, if the light measurement inside the vessel is representative of a too high biomass concentration, the control module can initiate biomass harvesting.

2. Features of the Photo-Bioreactor

2.1. Case of Continuous Light Radiation

Various aspects relating to a dimensioning of the bioreactor allowing the optimal use of the luminous flux resulting from the lighting devices will now be described. This dimensioning of the bioreactor is carried out by considering a continuous light supply, that is to say by considering that each light source 22 generates continuous light radiation of constant intensity over time.

2.1.1. Photon Capture Model

To understand if the flux of photons from the lighting devices is used optimally by the mass to be treated, it is proposed to use a model on the capture of photons by microalgae according to an emission surface and a geometry of the reactor.

The following representation shows the adjustable parameters for deducing productivities in a photo-bioreactor. Here it will be preferable to reduce the unilluminated fraction of the reactor as much as possible and to increase the surface receiving the photon flux.

The global model of the surface yield of a photo-bioreactor is as follows:

$$\langle r'_x \rangle_{max} \cong (1 - f_d)\rho_M \overline{\phi'} a_{light} \frac{K}{\left(\frac{\overline{n}+2}{\overline{n}+1}\right)q_0} \ln\left[1 + \frac{\left(\frac{\overline{n}+2}{\overline{n}+1}\right)q_0}{K}\right]$$

-continued $$= (1 - f_d)\rho_M \overline{\phi'} \langle A \rangle_{max} \frac{K}{\left(\frac{\overline{n}+2}{\overline{n}+1}\right)q_0} \ln\left[1 + \frac{\left(\frac{\overline{n}+2}{\overline{n}+1}\right)q_0}{K}\right]$$

where:
$f_d$ is the volume fraction unilluminated by design of the reactor ($f_d$=0 if the entire surface of the reactor is illuminated);

$\rho_M$ is the maximum energy yield of conversion of light energy into physico-chemical energy;

$\phi$ is the molar quantum yield of photosynthesis;

$\alpha$ is the linear diffusion modulus;

$a_{light}$ is the illuminated specific surface of the reactor on the volume;

K corresponds to a half-saturation constant of photosynthesis (depends on the microorganism);

ñ corresponds to the average degree of collimation of the incident radiation;

$Q_n$ is the average flux density on the surface of the photo-bioreactor.

The maximum performance of a photo-bioreactor can be characterized by some simplifications of the constants in an ideal case. Therefore, production will depend on the following elements:

The dark fraction «$S_x$», which corresponds to the unilluminated volume ratio ($f_d$=0):

$$Sx = (1 - f_d)\ln\left(1 + \frac{q}{K}\right) \text{ in } kg/m^2/d$$

Where q is expressed in $\mu molphotons/s/m^2$, and where K is the photosynthesis half-saturation constant (30000 $\mu mol/kgx/s$), The surface production "Px" due to the capture of the surface photon flux captured:

Px=Sx*aLight in $kg/m^3/d$ With corrective factor of 20%

The volume production according to the captured surface photon flux compared to the total volume:

$$a_{Light} = \frac{Slight}{Vr}.$$

By applying the previous calculation rules for:
an acrylic plate 0.2 m wide and 0.4 m length
an incident light of 250 $\mu mol/m2/s$,
a total reactor volume of 0.008 $m^3$,
no shadow zone (fd=0),
then the maximum theoretical volume productivity is estimated at 100 mg/L/d, as illustrated by the table below.

| Reactor geometry case | | |
|---|---|---|
| Length | 0.40 | m |
| Width | 0.20 | m |
| Illuminated area | 0.08 | $m^2$ |
| $Q_n$ | 250.00 | $\mu mol/m^2/s$ |
| K | 30000.00 | $\mu mol/kg_x/s$ |
| $V_r$ | 0.008 | $m^3$ |
| $a_{light}$ | 10 | $m^1$ |
| $f_d$ | 0.00 | Nd |
| $S_x$ | 0.01 | $Kg/m^2/d$ |

-continued

| Reactor geometry case | | |
|---|---|---|
| $P_x$ | 0.08 | Kg/m$^3$/d |
| $P_x$ correction | 0.099585634 | Kg/m$^3$/d |
| Theoretical max production | 100 | mg/L/d |

This is confirmed during an experiment using the reactor illustrated in FIG. 5, in which the lighting device comprises an acrylic plate disposed under the bottom of a vessel with transparent walls. An average production is 102 mg/L/d over 140 hours is obtained (minimum: 60 mg/L/d, maximum: 130 mg/L/d), as shown in FIG. 6.

Adding air with 2% $CO_2$ ensures mixing and brings carbon to the mass to be treated.

2.1.2. Determination of an Optimal Plate Surface Area for the Reactor Lighting Devices The purpose is to determine the optimal diffusion surface area of the luminous flux for the reactor. Of course, the number and arrangement of lighting devices can vary depending on the amount of biomass that is to be produced.

If it is sought to produce 1 kg of biomass per m$^3$ of culture in a volume of 100 m$^3$ by applying the formulas of the global modeling described in point 2.1, the lighting devices must comprise 2500 m$^2$ of luminous plates (light diffusers) emitting 1000 μmol/m$^2$/s (light sources).

This number is directly related to the desired yield, volume, geometry and light intensity.

The following table is obtained:

| | | |
|---|---|---|
| Light surface | 2 500 | m$^2$ |
| $Q_n$ | 1000.00 | μmol/m$^2$/s |
| K | 30000.00 | μmol/kgx/s |
| $V_r$ | 100.00 | m$^3$ |
| $a_{light}$ | 25.00 | m$^1$ |
| $f_d$ | 0.00 | nd |
| $S_x$ | 0.03 | Kg/m$^2$/d |
| continuous $P_x$ | 0.82 | Kg/m$^3$/d |
| Corrected yield | 0.98 | Kg/m$^3$/d |

2.1.3. Determination of a Maximum Amount of Biomass not to be Exceeded

The purpose is to determine the maximum concentration not to be exceeded so as not to have a dark zone in the medium (that is to say to maintain an $f_d$=0), Assume a reactor as shown in FIG. 7 and comprising:

a vessel having the following dimensions: 17 meters×2 meters×3 meters (Length×width×Height in meters), and a volume of 100 m$^3$ lighting devices including plates having dimensions of 3 meters×2 meters×0.01 meter (Length×width×Thickness).

To have a luminous surface of 2500 m$^2$, the number of plates must be 2500/(3×2)=417 plates, for a total thickness of 4.17 meters (the thickness of each plate being 1 centimeter).

In order to minimize the space requirement relating to the introduction of the plates into the vessel, each lighting device can comprise two plates joined by their rear faces so that their front faces are opposite one another (the rear faces of the two plates extending opposite each other and being in contact). An example of such a lighting device is shown in FIG. 4. The distance between the different lighting devices is then given by the following formula:

$$d=(L-E_{tot})/(\tfrac{1}{2}\times Nb_{Plates})$$

$$d=(17-4.17)/(\tfrac{1}{2}\times417).$$

where:

d is the free distance between the front faces of two successive lighting devices, L corresponds to the length of the vessel, $E_{tot}$ corresponds to the total thickness of the plates of the lighting devices (that is to say the sum of the thicknesses of the plates), $Nb_{Plates}$ corresponds to the number of plates required to have a luminous surface of 2500 m$^2$.

The following tables summarize the different results above.

| Characteristic reactor | |
|---|---|
| Length-m | 17 |
| Width-m | 2 |
| Depth-m | 3 |
| Volume-m3 | 100 |

| Characteristics of the plates | |
|---|---|
| Number of single plates | 417 |
| Thickness "$\tfrac{1}{2}$e" of a plate-m | 0.01 |
| Total thickness-m | 4.17 |
| Distance "D" between the rear faces of two successive lighting devices-m | 0.08 |
| Free space "d" between plates-m | 0.06 |

In order not to have a dark zone in the middle (that is to say to maintain an $f_d$=0), it is necessary to have a sufficient flux of photons (F) up to the middle zone (B) between two adjacent lighting devices.

The luminous intensity as a function of the distance Z can be expressed using the following formula:

$$I(z)=I_0 \cdot e^{-ka \cdot B \cdot z}$$

where:

$I_0$ corresponds to the incident light, $K_a$ is an absorption coefficient,

B corresponds to the biomass concentration,

Z corresponds to the length of the vessel.

FIG. 8 illustrates the maximum concentration of microalgae as a function of a distance between two adjacent lighting devices. If it is considered that from 50 μmol/m$^2$/s, the amount of light is insufficient to obtain satisfactory yields, it is possible to determine the maximum concentration not to be exceeded.

In the case of the device illustrated in FIG. 7 (and considering a free space "d" of 6 centimeters between the lighting devices), with a middle zone B located at 0.03 meters from each lighting device, the maximum concentration that should not be exceeded is 1.5 g/L.

This concentration can be measured using suspended solid sensors such as: 6131 Blue-Green Algae Sensor or ALS-OD4.

2.1.4. Determination of a $CO_2$ Load

The amount of $CO_2$ must be provided so as to correspond to the proportion of photons provided (Provide as much $CO_2$ as photons provided by the reactor).

Consequently, the flow rate of the mix (Air/$CO_2$) must be adjusted to the light choice selected. Here for 1 kg/m$^3$/d it takes 90% $CO_2$ with a flow rate of 4.77 m$^3$/h.

| Case of Culture condition $CO_2$ | | |
|---|---|---|
| $CO_2$ input | 90.00% | % |
| Flow rate | 4.77 | m³/h |
| $CO_2$ load | 202.38 | Kg $CO_2$/d |
| Assimilation | 2.059 | kgCO$_2$/kg$_{biomass}$ |
| Max production | 98.30 | Kg$_{alga}$/d |
| Volume | 100.00 | m³ |
| Maximum yield | 0.983 | kg/m³/d |

2.1.5. Plate Specificity

The person skilled in the art will know how to choose the right type of plate for each light diffuser. He will prioritize:

The type of etching (type V . . . ) which allows photons to be optimally transmitted over the entire plate, The material with the best light propagation rate for the transmission panel that receives the etchings (acrylic, polycarbonate, . . . ), An optimal reflection material to obtain the strongest luminosity, The most effective material for the homogenization of the photon flux.

The person skilled in the art will choose the positioning of the LEDs on one, two, three or four sides of each plate, as well as the shape (rectangle, square, cylindrical) of each plate according to the culture conditions. He will favor the most uniform LEDs in order to fill the entire edge of the etched plate.

2.2. Case of Discontinuous Light Radiation

Various aspects relating to a dimensioning of the bioreactor will now be described by considering a discontinuous light supply, that is to say by considering that each light source 22 generates a discontinuous light radiation composed of a close alternation of dark phases and of illuminated phases (flashes), for example at a frequency comprised between 10 and 50 KHz.

As an indication, FIG. 9 illustrates the difference between a discontinuous lighting 31 and a continuous lighting 32.

Such a discontinuous light supply allows to act positively on the culture yield in terms of biomass. As illustrated below, the transition from a continuous light supply to a discontinuous light supply allows to increase the distance between two adjacent light diffusers 21 (comprised between 2 and 10 centimeters, preferably between 4 and 8 centimeters, and even more preferably substantially equal to 6 centimeters), while maintaining the other parameters identical to those calculated previously.

2.2.1. Calculation of an Optimal Distance Between Adjacent Lighting Devices

Consider a system with a continuous average intensity of 1000 $\mu$mol·m$^{-2}$·s$^{-1}$ at the light diffusers 21.

When this average (continuous) intensity is parameterized in "flashes" while maintaining an average irradiance of 1000 $\mu$mol·m$^{-2}$·s$^{-1}$, it is then possible to obtain flash waves of 10000 $\mu$mol·m$^{-2}$·s$^{-1}$:

The cycle time $t_{cycle}$ is such that:

$t_{cycle}=t_{light}+t_{dark}$(s)/or the frequency (Hz)

where $t_{light}$ corresponds to a lighted phase and $t_{dark}$ corresponds to a dark phase;

The light fraction $\phi$ is such that: $\phi=(t_{light}/(t_{light}+t_{dark}))$

Integrated irradiance: $I_m=I_f\cdot\phi$ with $\phi$=10%;

$I_m$=1000 $\mu$mol·m$^{-2}$·s$^{-1}$ $I_m=I_f\cdot\phi\mu$mol·m$^{-2}$·s$^{-1}$ $I_f$=10000 $\mu$mol·m$^{-2}$·s$^{-1}$ This wave of photons allows to increase the entry distance of the photons into the medium, and therefore to increase the distance between the light diffusers 21 with an identical biomass concentration.

As shown in FIG. 10 illustrating microalgae concentration curves 33, 34 as a function of a distance between two adjacent lighting devices:

in the case of continuous lighting on the one hand (curve referenced 33), and in the case of discontinuous lighting (curve referenced 34) on the other hand, the middle distance can then be extended to 0.055 meters in flash with a concentration of 1.5 g/L. In other words, the lighting devices can be arranged so that the distance between two adjacent light diffusers 21 is substantially equal to 11 centimeters.

3. Other Embodiments

In the preceding description, different variants of bioreactors have been described, in particular bioreactors intended for industrial applications allowing the treatment of the gases emitted. Of course, the teachings of the present invention are not limited to large bioreactors intended for industrial applications.

In particular, in a variant embodiment, the bioreactor can be of smaller dimensions. For example, the bioreactor may comprise:

a vessel with transparent or translucent walls:

of length comprised between 1 and 10 meters, of width comprised between 50 centimeters and 5 meters, of thickness comprised between 4 and 30 centimeters, a single lighting device integrated into the vessel, an injection system including one (or more) diffusion units.

Such a bioreactor can in particular be used in urban applications to replace certain existing panels such as one (or more) wall(s) of an Abribus®, or of any bus shelter type.

Of course, the shape of the vessel is not necessarily parallelepipedal, and depends on the intended application (cylindrical shape, etc.). Similarly, for some applications the walls of the vessel may not be transparent or translucent.

In all cases, the lighting device is preferably disposed in the vessel so as to extend:

parallel to the side walls of the larger vessel, (including a light diffuser made up of a pair of plates, and At equal distance from said side walls of larger dimensions.

Such a lighting device comprises a light diffuser preferably composed of a pair of micro-etched plates joined by their rear faces, said plates having substantially the same shapes and dimensions as the side walls of larger dimensions of the vessel (plate dimensions=90-100% side wall dimensions of larger dimensions). The lighting device also comprises a light source as described above.

Preferably, the dimensions of the vessel are adapted so that the illumination of the mass to be treated by the lighting device is optimal. In particular, the distance separating:

the light diffuser and each larger side wall of the vessel can be comprised between 1 and 15 centimeters, preferably between 2 and 10 centimeters, and even more preferably between 3 and 6 centimeters.

4. CONCLUSIONS

The solution described above allows to increase the energy and biomass production yields of the reactor, in particular thanks to a homogeneous conduction of light, and to an optimal dimensioning of the various components of the reactor according to the maximum amount of biomass desired in the reactor.

This is valid for cultures in mixotrophy, in autotrophy on photosynthetic organisms but also for cultures in predominantly heterotrophic mixotrophy where light is not important for photosynthetic activity but for example for the induction of molecules of interest such as pigments (WO2017050917), and/or oil.

The invention presented above has many applications, and can for example be used to create a carbon sink allowing, by absorption of the carbon contained in the atmosphere (carbon monoxide/dioxide), to reduce the amount of atmospheric carbon dioxide.

The reader will have understood that many modifications can be made to the invention described above without materially departing from the new teachings and advantages described here.

For example, in the preceding description, the lighting and heating device was integrated into a reactor including a rotating assembly intended to ensure mixing this mass of microorganisms. It is obvious to the person skilled in the art that the lighting and heating device described above could be integrated into a reactor without a rotating assembly.

Accordingly, all such modifications are intended to be incorporated within the scope of the appended claims.

The invention claimed is:

1. A reactor including a vessel for containing:
a mass to be treated,
at least one lighting device configured to promote the treatment of the mass, and
a plurality of light diffusers, wherein two adjacent light diffusers in the plurality of light diffusers are spaced apart by a distance of between 2 and 10 centimeters, wherein each lighting device comprises:
   a light diffuser including at least one micro-etched plate transparent to light radiation and having opposite rear and front faces and at least two edges between the rear and front faces, wherein the area of each face is greater than an area of each edge, and wherein the rear face includes a plurality of micro-patterns, and a pitch between two adjacent micro-patterns of the plurality of micro-patterns of between 100 and 900 μm and greater than or equal to 100 μm, and
   a light source configured to generate the light radiation, wherein the light source is disposed on at least one edge of the plate and is oriented so that the generated light radiation propagates in the plate.

2. The reactor according to claim 1, wherein the at least one micro-etched plate is substantially flat and comprises four edges, wherein each light source includes a plurality of light-emitting diodes disposed on at least one of the smallest edges.

3. The reactor according to claim 2, wherein the diodes of the plurality of light-emitting diodes are disposed on the edge of the plate furthest from the bottom of the vessel.

4. The reactor according to claim 1, wherein the at least one micro-etched plate is cylindrical and comprises two edges, and wherein each light source includes a plurality of light-emitting diodes disposed on at least one of the two edges.

5. The reactor according to claim 1, wherein each light diffuser comprises a pair of micro-etched plates arranged so that their rear faces extend opposite one another.

6. The reactor according to claim 1, wherein each light diffuser further comprises at least one layer of material reflecting the light radiation, each layer of reflective material extending over the rear face of a respective plate.

7. The reactor according to claim 1, wherein each light diffuser further comprises at least one transmission layer, each layer of transmission material extending over the front face of a respective plate.

8. The reactor according to claim 1, wherein the light source of each lighting device is configured to generate a continuous light radiation.

9. The reactor according to claim 1, comprising a plurality of light diffusers, wherein two adjacent light diffusers are spaced apart by a distance comprised between 8 and 150 centimeters.

10. The reactor according to claim 9, wherein the light source of each lighting device is configured to generate discontinuous light radiation in the form of flashes composed of alternating dark phases and illuminated phases.

11. The reactor according to claim 9, wherein two adjacent light diffusers are spaced apart by a distance comprised between 10 centimeters and 50 centimeters.

12. The reactor according to claim 9, wherein two adjacent light diffusers are spaced apart by a distance substantially equal to 11 centimeters.

13. The reactor according to claim 1, wherein the vessel has a capacity of 100 m$^3$, and wherein the surface covered by the plates of the light diffusers is comprised between 2000 m$^2$ and 3000 m$^2$.

14. The reactor according to claim 13, wherein the surface covered by the plates of the light diffusers is comprised between 2250 m$^2$ and 2750 m$^2$.

15. The reactor according to claim 13, wherein the surface covered by the plates of the light diffusers is substantially equal to 2500 m$^2$.

16. The reactor according to claim 1, wherein the lighting devices are composed of:
   a first group of lighting devices with a first height, and
   a second group of lighting devices with a second height lower than the first height, and
   wherein a lighting device of the second group is disposed between two successive lighting devices of the first group.

17. The reactor according to claim 1, further comprising an injection system including a plurality of diffusion units, each diffusion unit:
   extends between two adjacent light diffusers, and
   is separated from the other diffusion units by at least two successive light diffusers.

18. The reactor according to claim 1, wherein each lighting device is independently connected to an electrical power supply module so that each lighting device can be removed individually from the reactor during its operation.

19. The reactor according to claim 1, wherein two adjacent light diffusers are spaced apart by a distance comprised between 4 centimeters and 8 centimeters.

20. The reactor according to claim 1, wherein two adjacent light diffusers are spaced apart by a distance substantially equal to 6 centimeters.

* * * * *